United States Patent [19]

Ichikawa et al.

[11] Patent Number: 4,864,856
[45] Date of Patent: Sep. 12, 1989

[54] LIQUID LEVEL DETECTING DEVICE

[75] Inventors: Koji Ichikawa; Norikazu Soga; Hirofumi Ohnishi, all of Kanagawa, Japan

[73] Assignee: Fuji Photo Film Co., Ltd., Kanagawa, Japan

[21] Appl. No.: 73,131

[22] Filed: Jul. 14, 1987

[30] Foreign Application Priority Data

Jul. 14, 1986 [JP] Japan ............................ 61-164897
Oct. 16, 1986 [JP] Japan ............................ 61-246146
Jan. 12, 1987 [JP] Japan ............................ 62-4556
Jan. 12, 1987 [JP] Japan ............................ 62-4557

[51] Int. Cl.$^4$ ............................ G01F 23/28
[52] U.S. Cl. ............................ 73/290 V; 73/864.25; 73/864.34
[58] Field of Search ............ 73/290 V, 291, 294, 73/864.24, 864.25, 864.34; 340/621, 618; 310/316, 321, 323, 351; 367/908

[56] References Cited

U.S. PATENT DOCUMENTS

| | | | |
|---|---|---|---|
| 3,246,516 | 4/1966 | Maropis | 73/290 V |
| 3,635,094 | 1/1972 | Oberli | 73/864.24 |
| 4,123,753 | 10/1978 | Gravert | 340/621 |
| 4,228,831 | 10/1980 | Kerns | 73/864.25 |
| 4,598,596 | 7/1986 | Wiseman et al. | 73/864.25 |

FOREIGN PATENT DOCUMENTS 21677 6/1978 Japan.
164356 7/1980 Japan.

Primary Examiner—Allan N. Shoap
Assistant Examiner—Patrick R. Scanlon
Attorney, Agent, or Firm—Sughrue, Mion, Zinn Macpeak & Seas

[57] ABSTRACT

A liquid level detecting device comprises a vibrator for vibrating a sample vessel containing a sample solution, and a piezo-electric element provided on a suction member having an opening for sucking the sample solution. Changes in the output voltage of the piezo-electric element are read out as the suction member is moved vertically, contact of the lower end of the suction member with the sample solution is detected based on the changes in the output voltage, and the liquid level of the sample solution is detected. Or, the liquid level detecting device comprises a vibration transmitting plate for holding a nozzle member to a suction member, a vibrator for vibrating the nozzle member at a predetermined frequency, a frequency control circuit for changing the frequency of vibration, and a detector for detecting extreme values of the output voltage of the vibrator corresponding to changes in the frequency. The liquid level is detected based on changes in the extreme values.

13 Claims, 8 Drawing Sheets

LIQUID LEVEL DETECTING DEVICE

BACKGROUND OF THE INVENTION

1. Field of the Invention

This invention relates to a liquid level detecting device for detecting the liquid level of a sample solution in the course of sucking up the sample solution in a vessel by use of a suction member. This invention particularly relates to a liquid level detecting device for use in an apparatus for automatically applying a predetermined amount of a sample solution onto a chemical analysis slide provided with a predetermined reagent layer.

2. Description of the Prior Art

Qualitative or quantitative analysis of a specific chemical constituent in a liquid sample is widely conducted for various industrial purposes. Particularly, it is very important in the biochemical and clinical fields to quantitatively analyze chemical constituents or physical constituents in body fluid such as blood or urine.

In recent years, as disclosed in, for example, Japanese Patent Publication No. 53(1978)-21677 and Japanese Unexamined Patent Publication No. 55 (1980)-164356, there has been developed and put into practice a dry type chemical analysis slide for quantitatively analyzing a specific chemical constituent or a specific physical constituent contained in a sample solution simply by applying to the slide a droplet of the sample solution. With the chemical analysis slide, it is possible to analyze a sample solution more simply and more quickly than when the conventional wet type analysis method is used. Therefore, the use of the chemical analysis slide is desirable particularly in medical institutions, research laboratories, or the like where many samples have to be analyzed.

When a chemical constituent or the like contained in a sample solution is to be analyzed by use of the chemical analysis slide, a measured amount of the sample solution is put on the chemical analysis slide and is maintained at a predetermined temperature (i.e. incubated) for a predetermined time in an incubator to cause a color reaction, and the reflection optical density is measured by exposing the chemical analysis slide to measuring light having a wavelength selected in advance in accordance with the combination of the constituent of the sample solution and the reagent contained in the reagent layer of the chemical analysis slide. In this manner, it is possible to achieve quantitative analysis of the chemical constituent or the like.

In the case where the aforesaid analysis is to be carried out, a predetermined amount of the sample solution must be measured accurately and applied to the reagent layer of the chemical analysis slide. This is because, if the amount of the sample solution applied differs from the predetermined amount, the optical density of the reflected light becomes different from the correct value, and the accuracy of the analysis is degraded. Accordingly, various pipettes have heretofore been proposed for accurately applying a predetermined amount of the sample solution when the sample solution is to be applied. For example, one of the proposed pipettes is constituted so that an application tip is fitted to a lower end of the pipette, a predetermined amount of a sample solution is sucked into the application tip, and then the predetermined amount of the sample solution is applied from the application tip onto a reagent layer of a chemical analysis slide. In general, with such a pipette, the predetermined amount of the sample solution is sucked into the application tip and discharged therefrom by use of a piston and cylinder mechanism. When the sample solution is to be sucked into the application tip and discharged onto the reagent layer by use of the pipette, the lower end of the application tip is first inserted into the sample solution, the predetermined amount of the sample solution is sucked in and kept in the application tip by use of a piston and cylinder mechanism or the like, then the lower end of the application tip is positioned above the reagent layer of the chemical analysis slide, and the sample solution in the application tip is applied onto the reagent layer by use of the piston and cylinder mechanism. However, in this case, when the lower end of the application tip is inserted into the sample solution and then pulled out therefrom for sample application, the sample solution is also taken up on the outer circumferential portion of the lower end of the application tip and applied onto the reagent layer together with the sample solution sucked in the application tip. As a result, error arises with the amount of the sample solution applied to the reagent layer, and the accuracy of measurement is degraded.

In order to eliminate the aforesaid problems, after the sample solution is sucked into the application tip by the pipette, the sample solution taken up on the outer circumferential portion of the lower end of the application tip has heretofore been wiped off, and then the sample solution sucked in the application tip is applied onto the reagent layer. However, in this case, a wiping operation is necessary and the operation efficiency becomes low. Also, when sample application is to be carried out automatically, it is not always possible to achieve the wiping operation automatically.

In order to solve the aforesaid problems, the applicant proposed an automatic sample applying apparatus constituted so that, when a sample solution is sucked into an application tip, the vertical position of the application tip and the liquid level of the sample solution are controlled to always make constant the insertion distance of the lower end of the application tip into the sample solution and to always make constant the amount of the sample solution taken up on the outer circumferential portion of the lower end of the application tip, thereby to always make constant the amount of the sample solution applied to the reagent layer of a chemical analysis slide. In this case, in order to make constant the insertion distance of the lower end of the application tip into the sample solution, it is necessary to accurately detect the position of the lower end of the application tip and the liquid level of the sample solution. However, in general, the application tip is frequently exchanged with a new application tip for preventing the sample solution from being mixed with a different sample solution, for hygienic reasons, or the like. Also, in general, the dimensional accuracy of the application tip is not so high, and application tips having different shapes may be used. Accordingly, it is not always possible to accurately detect the position of the lower end of the application tip fitted to the lower end of the pipette, and to control the insertion distance of the lower end of the application tip into the sample solution. Also, regarding the liquid level of the sample solution, it is not easy to accurately detect the liquid level in the case where, for example, bubbles are present on the surface of the sample solution.

SUMMARY OF THE INVENTION

The primary object of the present invention is to provide a liquid level detecting device which accurately detects the insertion distance of a lower end of a suction member into a liquid.

Another object of the present invention is to provide a liquid level detecting device which quickly detects the liquid level.

A further object of the present invention is to provide a liquid level detecting device which reliably and quickly detects the liquid level.

The present invention provides, in a sample solution sucking apparatus comprising a sample vessel containing a sample solution, a suction member disposed above the sample vessel and having a suction opening at a lower end, a vertical position control means for vertically moving the suction member, and a suction means communicating with the suction member for sucking the sample solution via the suction opening when the suction member is moved down by the vertical position control means and the lower end of the suction member is inserted into the sample solution,
a liquid level detecting device comprising:
  (i) a vibration imparting means for imparting vibration to said sample vessel, and
  (ii) a piezo-electric element provided on said suction member or on said suction means,
whereby a change in an output voltage of said piezo-electric element is read out as said suction member is moved vertically by said vertical position control means, contact of the lower end of said suction member with said sample solution is detected on the basis of the change in said output voltage, and the liquid level of said sample solution is detected.

The present invention also provides, in a sample solution sucking apparatus comprising a sample vessel containing a sample solution, a suction member disposed above the sample vessel and having a nozzle member for suction at a lower end, a vertical position control means for vertically moving the suction member, and a suction means communicating with the nozzle member for sucking the sample solution via the nozzle member when the suction member is moved down by the vertical position control means and the nozzle member at the lower end of the suction member is inserted into the sample solution,
a liquid level detecting device comprising:
  (i) a vibration transmitting plate for holding said nozzle member to said suction member and capable of being vibrated,
  (ii) a vibration imparting means for imparting vibration having a predetermined frequency to said nozzle member held by said vibration transmitting plate,
  (iii) a frequency control circuit for changing the frequency of vibration imparted by said vibration imparting means to said nozzle member, and
  (iv) an extreme value detecting means for detecting an output voltage or an output current of said vibration imparting means and detecting an extreme value of said output voltage or said output current corresponding to changes in said frequency,
whereby contact of said nozzle member with said sample solution is detected on the basis of a change in the extreme value detected by said extreme value detecting means, and the liquid level of said sample solution is detected.

The present invention further provides, in a sample solution sucking apparatus comprising a sample vessel containing a sample solution, a suction member disposed above the sample vessel and having a nozzle member for suction at a lower end, and a vertical position control means for vertically moving the suction member,
a liquid level detecting device comprising:
  (i) a vibration transmitting plate for holding said nozzle member to said suction member and capable of being vibrated,
  (ii) a vibration imparting means for imparting vibration having a predetermined frequency to said nozzle member held by said vibration transmitting plate,
  (iii) a frequency control circuit for operating said vibration imparting means to impart vibration sweeping within a predetermined frequency range,
  (iv) an extreme value detecting means for detecting changes in an impedance of said vibration imparting means and detecting an extreme value of said impedance corresponding to changes in the frequency within said predetermined frequency range, and
  (v) a sweep range contracting means for having the extreme value of the impedance of said vibration imparting means detected by having a sweep within a comparatively wide frequency range done by said frequency control means before said nozzle member contacts said sample solution, and contracting said predetermined frequency range, within which the sweep is effected by said frequency control circuit, to a narrow range including a frequency corresponding to said detected extreme value,
whereby contact of said nozzle member with said sample solution is detected and the liquid level of said sample solution is detected on the basis of a change in the extreme value detected based on the impedance value of said vibration imparting means at the time vibration sweeping within said narrow frequency range contracted by said sweep range contracting means is imparted.

The present invention also provides, in a sample solution sucking apparatus comprising a sample vessel containing a sample solution, a suction member disposed above the sample vessel and having a nozzle member for suction at a leading end, and a vertical position control means for vertically moving the suction member,
a liquid level detecting device comprising:
  (i) a vibration transmitting plate for holding said nozzle member to said suction member and capable of being vibrated,
  (ii) a vibration imparting means for imparting sine wave-like vibration having a predetermined frequency to said nozzle member held by said vibration transmitting plate,
  (iii) a frequency control circuit for changing the frequency of vibration imparted by said vibration imparting means to said nozzle member,
  (iv) an extreme value detecting means for detecting changes in an impedance of said vibration imparting means and detecting an extreme value of said impedance corresponding to changes in said frequency, and (v) a contact detecting means for detecting contact of said nozzle member with said sample solution on the basis of a change in the extreme value detected by said extreme value detecting means, and detecting the liquid level of said sample solution.

In the liquid level detecting device of the present invention, the kind of the sample solution, the shape of the suction member or the nozzle member, and the like are not limited to specific ones, and any sample solution and any suction member or nozzle member may be used. However, the liquid level detecting device in accordance with the present invention is advantageous particularly for detecting contact of an application tip as the suction member or the nozzle member (a nozzle body or an application tip fitted to the lower end of the nozzle body) with a sample solution and for detecting the liquid level of the sample solution to control the distance of insertion of the application tip or the lower end of the nozzle member into the sample solution when a predetermined amount of the sample solution is to be sucked into the application tip or the nozzle member in an automatic sample applying apparatus for applying the predetermined amount of the sample solution onto a reagent layer of a chemical analysis slide.

With the first mentioned liquid level detecting device in accordance with the present invention, vibration applied by the vibration imparting means to the sample vessel is transmitted to the suction member via the sample solution when the lower end of the suction member contacts the surface of the sample solution. As a result, the piezo-electric element provided on the suction member or on the suction means receives vibration and generates a high output voltage. Therefore, contact of the suction member with the sample solution can be detected by detecting the output voltage. In this case, even though bubbles are present on the surface of the sample solution, contact of the suction member with the surface of the sample solution can be detected accurately since there is a large difference between transmissibility of vibration via the bubbles and transmissibility of vibration via the liquid. Accordingly, the lower end of the suction member can be inserted to a predetermined depth in the sample solution by moving down the suction member by a predetermined distance from the position at which contact of the suction member with the sample solution is detected, and thus the distance of insertion of the lower end of the suction member into the sample solution can be controlled accurately and easily.

With the second mentioned liquid level detecting device in accordance with the present invention, vibration of the nozzle member (a nozzle body or an application tip) applied by the vibration imparting means receives resistance from the sample solution, and the output voltage or the output current of the vibration imparting means changes when the lower end of the nozzle member contacts the surface of the sample solution. The change in the output voltage or the output current can be detected as a change in the extreme value of the output voltage or the output current with respect to the frequency of imparted vibration, and contact of the nozzle member with the sample solution can be detected accurately. In this case, even when bubbles are present on the surface of the sample solution, contact of the nozzle member with the surface of the sample solution can be detected accurately since there is a large difference between the resistance by the bubbles and the resistance by the liquid. Accordingly, the lower end of the nozzle member can be inserted to a predetermined depth in the sample solution by moving down the nozzle member by a predetermined distance from the position at which contact of the nozzle member with the sample solution is detected. Particularly, in this case, since it is not necessary to detect the initial position of the lower end of the nozzle member and the initial liquid level of the sample solution, the size and the shape of the sample vessel and the amount of the sample solution introduced into the sample vessel are not limited. Also, in the case where a application tip is used as the nozzle means, the shape and dimensions of the application tip are not limited.

With the third mentioned liquid level detecting device in accordance with the present invention, before the nozzle member contacts the sample solution in the course of detecting the contact position of the nozzle member with the surface of the sample solution by downward movement of the nozzle member, vibration is applied to the nozzle member so as to sweep within a predetermined, comparatively wide sweep range, an extreme value of impedance at this time is detected, and the sweep range is adjusted to a narrow one including the frequency corresponding to the detected extreme value by the sweep range contracting means. Then, vibration sweeping within the narrow sweep range is given to the nozzle member, contact of the nozzle member with the sample solution is detected on the basis of a change in the extreme value of the output of the vibration imparting means at this time, and the liquid level of the sample solution is detected. In this case, since after the first sweep the range of the sweep is narrowed, the time required for each sweep becomes short and, as a result, the time required for detection of the liquid level is shortened. Since the first sweep is carried out within a predetermined, comparatively wide sweep range, the extreme value in each liquid level detection can be detected reliably by the sweep within the wide range even if the frequency corresponding to the extreme value is caused to vary when the application tip fitted to the lower end of the nozzle member is changed. On the other hand, after the extreme value has been detected by the first sweep, the change in the frequency corresponding to the extreme value is small even though the level of the extreme value changes when the nozzle member contacts the surface of the sample solution. Therefore, the change in the extreme value generated by contact of the nozzle member with the surface of the sample solution can be detected reliably by carrying out the sweep within the aforesaid narrow range.

With the fourth mentioned liquid level detecting device in accordance with the present invention, vibration of the nozzle member (a nozzle body or an application tip) applied by the vibration imparting means receives resistance from the sample solution, and the output voltage or the output current of the vibration imparting means changes when the lower end of the nozzle member contacts the surface of the sample solution. The change in the output voltage or the output current can be detected as a change in the extreme value of the output voltage or the output current with respect to the frequency of imparted vibration. Specifically, the extreme value is detected as a change in voltage in the case where a signal fed to a vibrator is supplied by a constant current source, and as a change in current in the case where the signal fed to the vibrator is supplied from a constant voltage source. Therefore, contact of the nozzle member with the sample solution can be detected by detecting a change in the impedance of the vibration imparting means and detecting the extreme value of the impedance corresponding to the change in the frequency. At this time, since sine wave-like vibration is utilized as the vibration applied by the vibration imparting means to the nozzle member, the change in the extreme value generated at the time the nozzle member contacts the surface of the sample solution becomes comparatively large, and can be detected easily. Accordingly, contact of the nozzle member with the surface of the sample solution can be detected reliably.

DESCRIPTION OF THE PREFERRED EMBODIMENTS

The present invention will hereinbelow be described in further detail with reference to the accompanying drawings.

Figure 1:
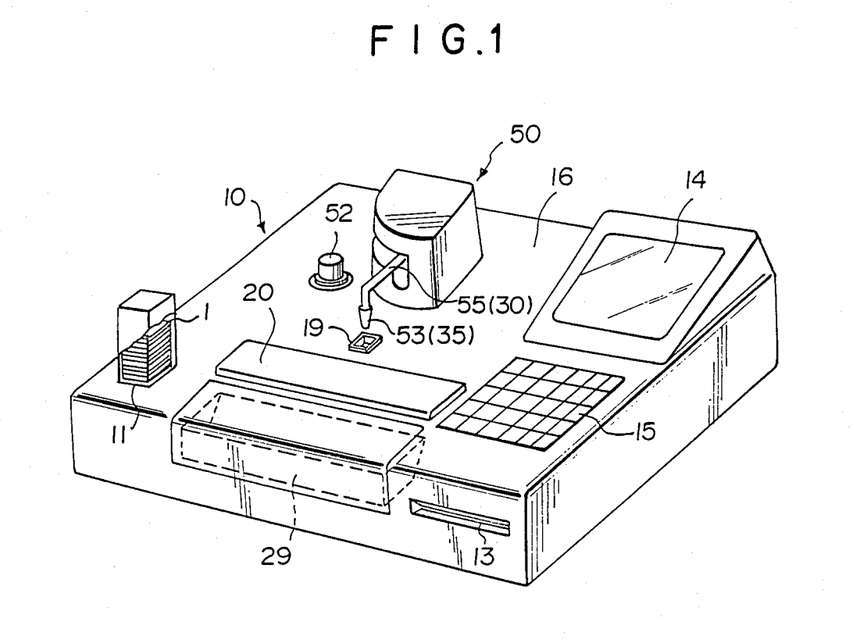
FIG. 1 is a perspective view showing a chemical analysis apparatus provided with an embodiment of the liquid level detecting device in accordance with the present invention.
Figure 2:
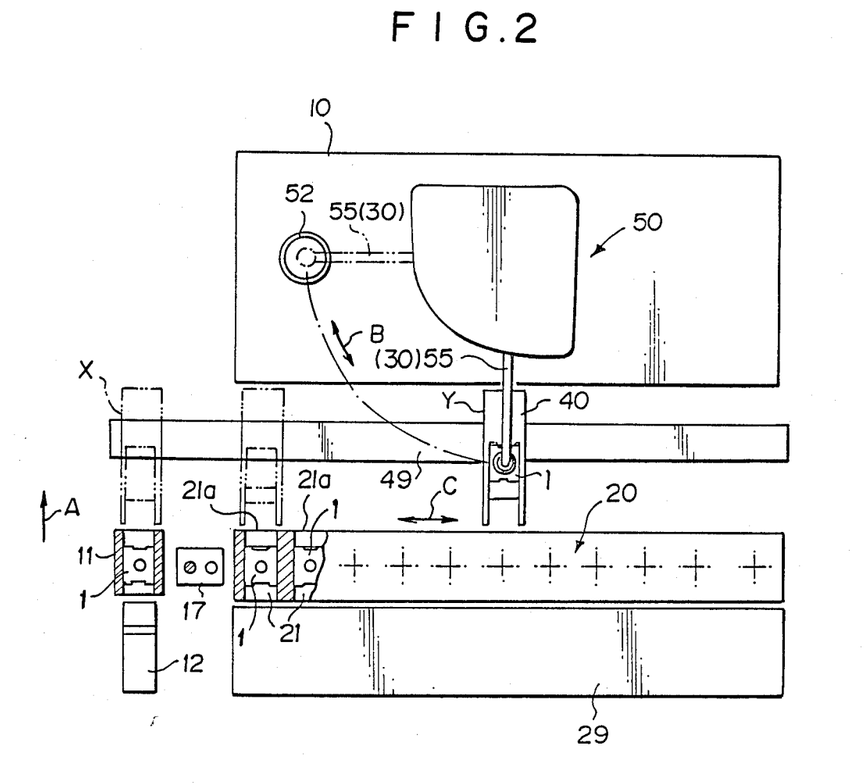
FIG. 2 is a plan view showing the chemical analysis apparatus shown in FIG. 1 with the cover plate removed.

FIG. 1 shows an example of a chemical analysis apparatus having an automatic sample applying apparatus 50 provided with an embodiment of the liquid level detecting device in accordance with the present invention. The chemical analysis apparatus comprises a cartridge 11, an incubator 20, a conveyance and feed-in means 40 (FIG. 2), and the automatic sample applying apparatus 50 provided on a main body 10. FIG. 2 is a plan view of FIG. 1 with a cover plate 16 removed from the main body 10. As shown in FIG. 1, this apparatus is also provided with a display section 14 for displaying the measured values in the course of measurement or the like, operating key section 15 for controlling the displaying of the measured values or the like, and a magnetic disk inserting section 13 for recording the measured values or the like on a magnetic disk, which are omitted for simplicity of explanation in FIG. 2.

The cartridge 11 houses a plurality of unused chemical analysis slides 1, 1, . . . stacked one upon another. The chemical analysis slides 1, 1, . . . in the cartridge 11 are pushed out rearwardly (in the direction as indicated by the arrow A in FIG. 2) by a pushing lever 12, one by one, starting from the bottom most chemical analysis slide 1. The incubator 20 is disposed on the rightward lateral side of the cartridge 11. A plurality of housing compartments 21, 21, . . . for housing the chemical analysis slides 1, 1, . . . are formed in the incubator 20 so that the chemical analysis slides 1, 1,. . . stand side by side on the same plane as the bottommost chemical analysis slide 1 in the cartridge 11. A receiving member 29 for receiving the used chemical analysis slides 1, 1, . . . ejected from the housing compartments 21, 21, . . . is disposed in front of the incubator 20. Further, a read-out head (not shown) for measuring the optical density of the reflected light and slideable in the transverse direction as indicated by the arrow C to face the lower surface of the incubator 20 is disposed below the incubator 20. The read-out head is slid on a rail extending in the transverse direction below the incubator 20 by, for example, a linear motor. The rail extends up to the position below the cartridge 11, and therefore the read-out head can be slid up to the position facing the lower surface of the cartridge 11 to face the bottommost chemical analysis slide 1 in the cartridge 11. Accordingly, the optical density of the light reflected by the chemical analysis slide 1 housed in each of the housing compartments 21, 21, . . . of the incubator 20 can be measured by the read-out head, and fog measurement for measuring the optical density of the light reflected by an unused chemical analysis slide 1 can be carried out by use of the read-out head.

The incubator 20 incorporates a heater (not shown) for incubating the chemical analysis slides 1, 1, . . . in the housing compartments 21, 21, . . . .. Each of the chemical analysis slides 1, 1, . . . comprises a frame having a circular hole for application of a liquid sample, and a dry type multi-layer film disposed in the frame and composed of a supporting material, a reagent layer, and a development layer, which are layered in this order. A predetermined amount of the sample material such as urine or blood is applied onto the film, and incubated in the incubator 20 for causing a color reaction.

On the other hand, the conveyance and feed-in means 40 is disposed at the rear of the incubator 20 to be slideable in the transverse direction as indicated by the arrow C to face inlet openings 21a, 21a, . . . of the housing compartments 21, 21, . . . .. The conveyance and feed-in means 40 is slid on a rail 49 extending in the transverse direction by a linear motor or the like along the incubator 20 and up to the position facing the cartridge 11 as indicated by the chain line X in FIG. 2. Therefore, the conveyance and feed-in means 40 slid to the position as indicated by the chain line X can receive the chemical analysis slide 1 pushed out by the pushing lever 12 from the cartridge 11, convey the chemical analysis slide 1 up to a predetermined position, and then feed the chemical analysis slide 1 into a predetermined housing compartment 21.

The automatic sample applying apparatus 50 has a sample application arm 55 rotatable in the direction as indicated by the arrow B in FIG. 2 and is disposed at the rear of the conveyance and feed-in means 40. An application tip 53 is releasably fitted to the lower end of the application arm 55. The lower end of the application arm 55 is rotatable in the direction as indicated by the arrow B between a sucking position as indicated by the chain line in FIG. 2 above a sample vessel 52 disposed on the main body 10 and a sample applying position as indicated by the solid line in FIG. 2 above a sample application hole 19 formed in the cover plate 16 on the main body 10. When the chemical analysis slide 1 received from the cartridge 11 is conveyed by the conveyance and feed-in means 40 up to a predetermined position as indicated by the solid line Y in FIG. 2 at which the sample solution is to be applied to the reagent layer of the chemical analysis slide 1, the reagent layer is disposed below the sample application hole 19. At the sample applying position, the lower end of the application tip 53 is disposed above the reagent layer of the chemical analysis slide 1. A predetermined amount of the sample solution can be sucked up from the sample vessel 52 into the application tip 53 at the sucking position, the sample application arm 55 can be rotated in the direction as indicated by the arrow B until the application tip 53 is disposed at the sample applying position, and then the sample solution can by applied from the application tip 53 to the reagent layer of the chemical analysis slide 1. Thereafter, the chemical analysis slide 1 is fed into an empty housing compartment 21 of the incubator 20, incubated therein, and the optical density of the light reflected by the chemical analysis slide 1 is read out to conduct chemical analysis of the sample solution. A white/black reference density plate 17 for elimination of measurement error of the read-out head is disposed between the incubator 20 and the cartridge 11.

The operations of the chemical analysis apparatus having the aforesaid configuration will be described hereinbelow.

First, the read-out head is moved to the position facing the lower surface of the cartridge 11, and fog measurement is carried out for the bottom most chemical analysis slide 1 among the chemical analysis slides 1, 1, ... stacked in the cartridge 11. In the course of movement of the read-out head, the read-out head once comes to stand facing the reference density plate 17, and measurement error is eliminated. After the fog measurement is carried out, the chemical analysis slide 1 is pushed by the pushing lever 12 onto the conveyance and feed-in means 40 moved to the position as indicated by the chain line X in FIG. 2, and held on the conveyance and feed-in means 40. The conveyance and feed-in means 40 is moved rightwardly on the rail 49 up to the position as indicated by the solid line Y below the sample applying position. Then, the sample solution in the sample vessel 52 is sucked by the automatic sample applying apparatus 50 into the application tip 53 at the sucking position, and the sucked sample solution is applied onto the reagent layer of the chemical analysis slide 1 conveyed to the position as indicated by the solid line Y at the sample applying position. The conveyance and feed-in means 40 is then moved on the rail 49 in the transverse direction as indicated by the arrow C to the position facing a predetermined housing compartment 21 of the incubator 20, and feeds the chemical analysis slide 1 into the housing compartment 21. The read-out head is moved to the position below the housing compartment 21, emits light to the chemical analysis slide 1 incubated in the incubator 20, and measures the optical density of the light reflected by the chemical analysis slide 1, thereby to carry out chemical analysis of the sample solution. When the measurement is completed, the chemical analysis slide 1 is ejected by the conveyance and feed-in means 40 from the housing compartment 21 to the receiving member 29. The aforesaid operations are thereafter repeated, and chemical analysis using many chemical analysis slides is carried out automatically and continuously.

The automatic sample applying apparatus 50 for automatically applying the sample solution in the sample vessel 52 to the reagent layer of the chemical analysis slide 1 in the course of carrying out the aforesaid measurement will hereinbelow be described in detail.

Figure 3:
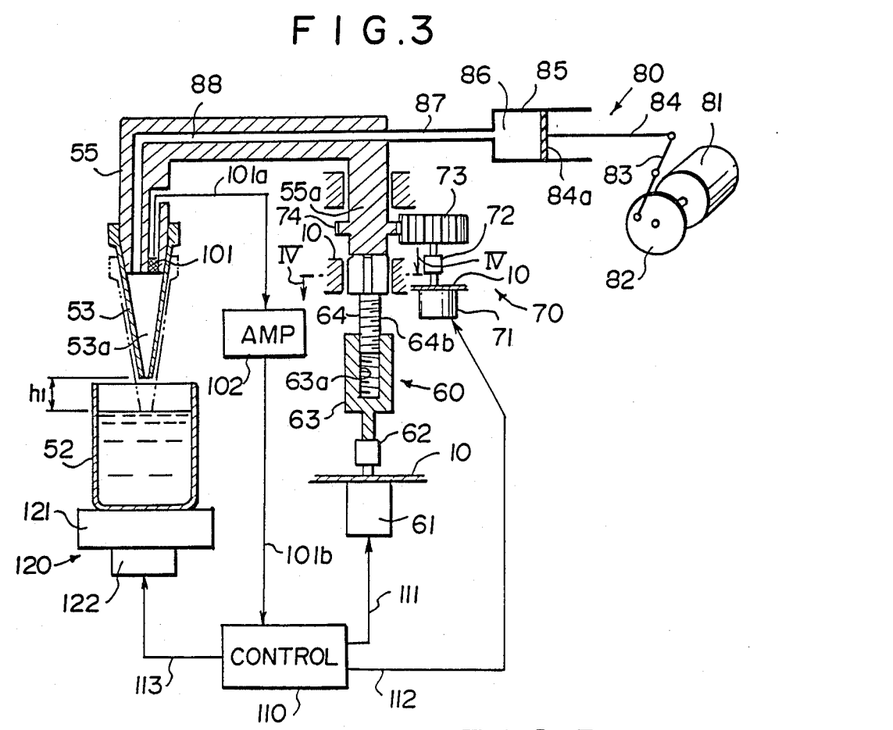
FIG. 3 is a schematic sectional view showing an example of the automatic sample applying apparatus constituting the chemical analysis apparatus shown in FIG. 1 and provided with the embodiment of the liquid level detecting device in accordance with the present invention.

The configuration of the automatic sample applying apparatus 50 is shown in FIG. 3. The automatic sample applying apparatus 50 is constituted by a vertical tip position control means 60 for vertically moving the sample application arm 55 and the application tip 53, a tip movement means 70 for rotating the sample application arm 55 and moving the application tip 53 between the sucking position and the sample applying position, a suction and discharge means 80 communicating with the application tip 53 and carrying out suction of the sample solution into the application tip 53 and discharging of the sample solution therefrom, and a vessel supporting means 120 for supporting the sample vessel 52.

Figures 4, 5:
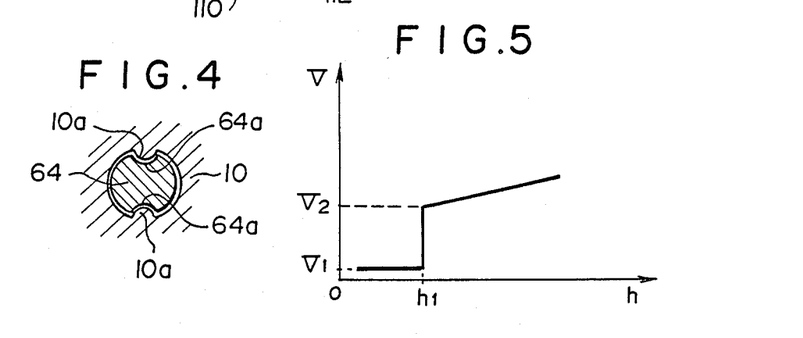
FIG. 4 is a sectional view taken along line IV—IV of FIG. 3.
FIG. 5 is a graph showing the relationship between the voltage generated by the piezo-electric element and the movement distance of the application tip.

The vertical tip position control means 60 is composed of a pulse motor 61 secured to the main body 10, a drive member 63 coupled with a rotation shaft of the pulse motor 61 via a coupling 62, and a driven member 64 having male threads 64b meshed with female threads 63a formed on the drive member 63. As illustrated in FIG. 4 showing a sectional view taken along line IV—IV of FIG. 3, the driven member 64 has recesses 64a, 64a loosely engaging with protrusions 10a, 10a of the main body 10 so that the driven member 64 is moveable vertically with respect to the main body 10 but cannot rotate. Also, a rotation shaft 55a of the sample application arm 55 is coupled with an upper portion of the driven member 64 so that they can rotate with respect to each other. Therefore, when the drive member 63 is rotated by the pulse motor 61, since rotation of the driven member 64 is prevented, the thread meshing amount between the driven member 64 and the drive member 63 changes, and the driven member 64 is moved vertically. At this time, the rotation shaft 55a of the sample application arm 55 coupled with the driven member 64 is also moved vertically.

The tip movement means 70 is composed of a swing motor 71 secured to the main body 10, a drive gear 73 coupled with a rotation shaft of the swing motor 71 via a coupling 72, and a driven gear 74 meshing with the drive gear 73 and moveable vertically with respect to the drive gear 73. The driven gear 74 is coaxially secured to the rotation shaft 55a of the sample application arm 55. The rotation shaft 55a of the sample application arm 55 is rotatably supported on the main body 10.

Therefore, when the swing motor 71 is operated, the rotation thereof is transmitted to the rotation shaft 55a via the coupling 72, the drive gear 73 and the driven gear 74. As a result, the sample application arm 55 is rotated around the rotation shaft 55a so that the application tip 53 fitted to the leading end of the sample application arm 55 is moved between the sucking position and the sample applying position.

The suction and discharge means 80 is composed of a piston drive motor 81 having a cam plate 82 on the rotation shaft thereof, a piston rod 84 coupled with the cam plate 82 via a link 83, a cylinder 85 in which a piston 84a secured to the leading end of the piston rod 84 is inserted, and a flexible hose 87 for making a space 86 in the cylinder 85 communicate with a passage 88 formed in the sample application arm 55 and communicating with a space 53a in the application tip 53. The rotating motion of the piston drive motor 81 is converted by the link 83 into a reciprocal motion of the piston rod 84, and a reciprocal motion of the piston 84a generated thereby causes the volume of the space 86 in the cylinder 85 to change. The changes in the volume of the space 86 are transmitted to the space 53a in the application tip 53 via the hose 87 and the passage 88. In this manner, suction of the sample solution into the space 53a in the application tip 53 and discharging of the sample solution therefrom are carried out.

The vessel supporting means 120 is composed of a supporting base 121 secured to the main body 10 for supporting the sample vessel 52 thereon, and a vibration imparting means 122 constituted by a microphone or the like for imparting vibration to the supporting base 121.

On the other hand, the leading end of the sample application arm 55 is provided with a piezo-electric element 101. The voltage generated by the piezo-electric element 101 is transmitted to an amplifier 102 via a line 101a, and the voltage amplified by the amplifier 102 is transmitted to a controller 110 via a line 101b. The controller 110 controls the operations of the pulse motor 61 and the swing motor 71 via a line 111 and a line 112, and operates the vibration imparting means 122 via a line 113 to apply predetermined vibration to the sample vessel 52 via the supporting base 121.

The operations of the automatic sample applying apparatus 50 having the aforesaid configuration will be described hereinbelow. First, the sample vessel 52 containing the sample solution is placed on the supporting base 121 of the vessel supporting means 120, and the vibration imparting means 122 is activated by the controller 110 via the line 113. As a result, the vibration imparting means 122 gives predetermined vibration to the sample solution in the sample vessel 52 via the supporting base 121. Also, the vertical tip position control means 60 is activated to move down the application tip 53 fitted to the leading end of the sample application arm 55 together with the sample application arm 55 at the sucking position. As shown in FIG. 3, when the application tip 53 is moved down by a distance h1, the lower end of the application tip 53 contacts the surface of the sample solution in the sample vessel 52. As a result, vibration transmitted from the vibration imparting means 122 to the sample solution is transmitted to the application tip 53 via the sample solution, and further transmitted from the application tip 53 to the piezoelectric element 101 via the leading end of the sample application arm 55. When the piezo-electric element 101 receives the vibration, the voltage generated thereby increases sharply. The change in the voltage generated by the piezo-electric element 101 is amplified by the amplifier 102, and detected by the controller 110, thereby to detect contact of the application tip 53 with the sample solution.

FIG. 5 shows the relationship between the downward movement distance h of the application tip 53 and tee voltage V generated by the piezo-electric element 101. As shown in FIG. 5, when the application tip 53 is not in contact with the sample solution, vibration given to the sample solution is not so much transmitted to the piezo-electric element 101, and the voltage V generated by the piezo-electric element 101 is equal to a voltage V1 which is nearly zero. However, when the application tip 53 is moved down by the distance h1 and the lower end thereof contacts the sample solution, the vibration is transmitted to the piezo-electric element 101 via the sample solution, and the voltage V generated by the piezo-electric element 101 increases sharply to V2. Therefore, the liquid level of the sample solution can be detected reliably by detecting the voltage V generated by the piezo-electric element 101, and reading out the position of the application tip 53 at the time the generated voltage V increases sharply. In this case, even if bubbles should be present on the surface of the sample solution and the liquid level of the sample solution is not visible easily for example, contact of the lower end of the application tip 53 with the sample solution can be detected reliably since transmissibility of vibration via the bubbles and transmissibility of vibration via the bubbles and transmissibility of vibration via the liquid differ markedly from each other.

Thereafter, the application tip 53 is moved down by a predetermined distance from the position at which it contacts the surface of the sample solution, and thus the lower end of the application tip 53 is inserted into the sample solution by the predetermined depth. The predetermined depth can be controlled on the basis of the voltage V changing in accordance with the depth of insertion of the lower end of the application tip 53 into the sample solution as shown in FIG. 5. In order to minimize the amount of the sample solution taken up by the outer circumferential portion of the lower end of the application tip 53, the predetermined depth should preferably be adjusted to be as small as possible. Then, the suction and discharge means 80 is activated to move the piston 84a and suck a predetermined amount of the sample solution into the space 53a of the application tip 53.

After the predetermined amount of the sample solution has been sucked into the space 53a inside of the application tip 53, the sample application arm 55 is moved up by the vertical tip position control means 60 and the application tip 53 is raised. Then, the sample application arm 55 is rotated around the rotation shaft 55a by the tip movement means 70, and the application tip 53 is moved from the sucking position to the sample applying position. The application tip 53 is then moved down by the vertical tip position control means 60 until the lower end of the application tip 53 comes above and near a reagent layer portion 1a of the chemical analysis slide 1. The sample solution in the application tip 53 is then gradually discharged by the action of the suction and discharge means 80, and a droplet of the sample solution is formed at the lower end of the application tip 53. The application tip 53 is moved down in this condition, and the droplet of the sample solution is applied to the reagent layer portion of the chemical analysis slide 1. Thereafter, the application tip 53 is moved up, and the application of the sample solution is completed.

Figure 6:
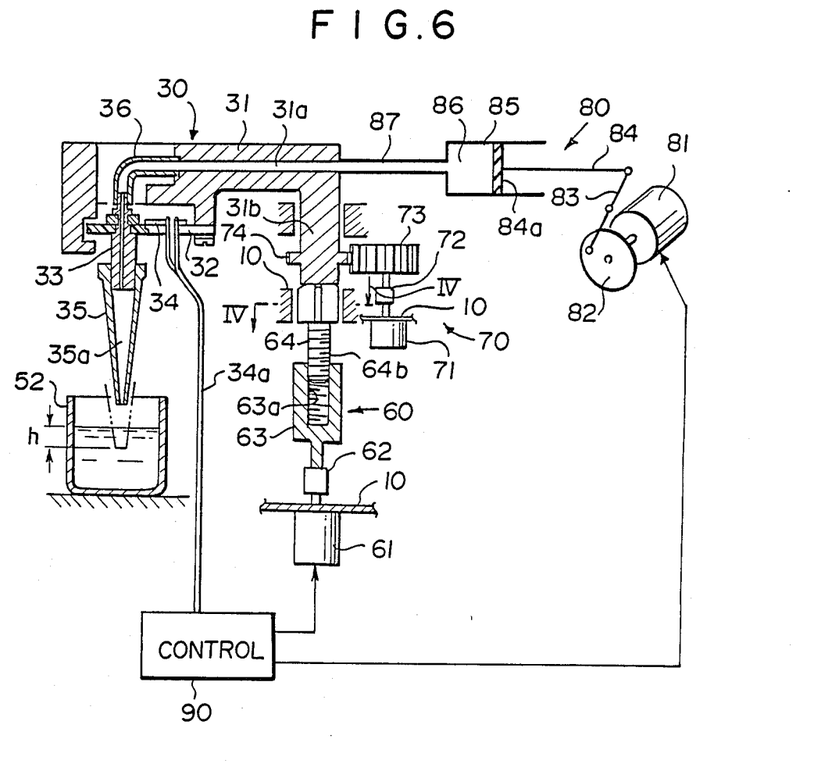
FIG. 6 is a schematic sectional view showing another example of the automatic sample applying apparatus constituting the chemical analysis apparatus shown in FIG. 1 and provided with another embodiment of the liquid level detecting device in accordance with the present invention.

FIG. 6 is a schematic sectional view showing another example of the automatic sample applying apparatus 50 constituting the chemical analysis apparatus shown in FIG. 1 and provided with another embodiment of the liquid level detecting device in accordance with the present invention. In FIG. 6, similar elements are numbered with the same reference numerals with respect to FIG. 3, except for a sample application arm 30, the parts thereof, an application tip 35, and a controller 90. The automatic sample applying apparatus 50 is constituted by the sample application arm 30 having a leading end to which an application tip 35 is fitted releasably, the vertical tip position control means 60 for vertically moving the sample application arm 30, the tip movement means 70 for rotating the sample application arm 30 and moving the application tip 35 between the sucking position and the sample applying position, and the suction and discharge means 80 communicating with the application tip 35 and carrying out suction of the sample solution into the application tip 35 and discharging of the sample solution therefrom.

The sample application arm 30 is composed of an arm body 31 rotatable around a rotation shaft 31b with respect to the main body 10, a vibration transmitting plate 32 capable of being vibrated and having one side supported on the arm body 31 at an end portion of the ar body 31 opposite to the rotation shaft 31b, a nozzle body 33 supported on the vibration transmitting plate 32, a vibrator 34 constituted of a piezo-electric ceramic material or the like and secured to the vibration transmitting plate 32, and the application tip 35 releasably fitted to the lower end of the nozzle body 33. The nozzle body 33 has a vertically extending through-hole. The lower end of the through-hole communicates with an internal space 35a of the application tip 35, and the upper end thereof communicates with a passage 31a formed through the arm body via a hose 36. The vibrator 34 vibrates upon application thereto of an electric signal applied from the exterior, thereby to vibrate the vibration transmitting plate 32. As a result, the nozzle body 33 supported by the vibration transmitting plate 32 and the application tip 35 fitted to the nozzle body 33 receive vibration having a frequency equal to the frequency of vibration of the vibration transmitting plate 32.

Figure 7:
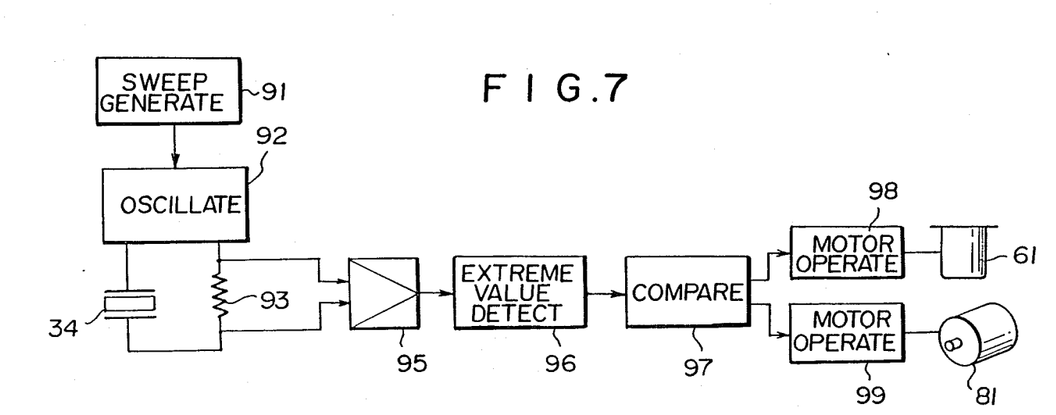
FIG. 7 is a block diagram showing the operation of a controller used in the embodiment of the liquid level detecting device shown in FIG. 6.
Figure 8:
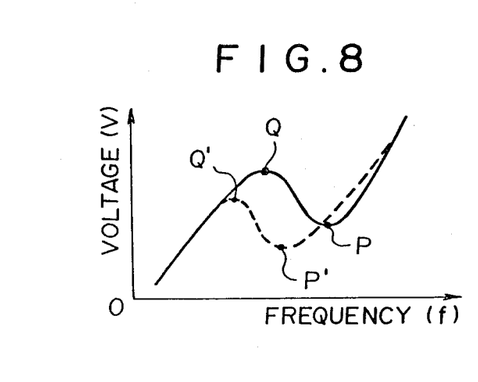
FIG. 8 is a graph showing the relationship between the frequency and the voltage detected in the embodiment of the liquid level detecting device shown in FIG. 6, FIGS. 9 and 10 are sectional views showing modified forms of the embodiment of the liquid level detecting device shown in FIG. 6.

The electric signal applied to the vibrator 34 is supplied by the controller 90. The operations of the controller 90 will be described below with reference to FIG. 7. The electric signal applied to the vibrator 34 is generated by a sweep generator 91 via a voltage control oscillator 92 so that the vibrator 34 vibrates with the frequency thereof changing to sweep within a predetermined frequency range, for example, within the range of 0 to 1 kHz. Specifically, a frequency control circuit is constituted by the sweep generator 91, the voltage control oscillator 92 and the vibrator 34 as shown in FIG. 7. Vibration of the vibrator 34 is transmitted to the nozzle body 33 and the application tip 35 via the vibration transmitting plate 32, and the nozzle body 33 and the application tip 35 vibrate in the same manner. The hose 36 is flexible, and therefore little vibration is transmitted from the hose 36 to the arm body 31. When the vibrator 34 vibrates in this manner, the voltage (V) across the ends of a fixed resistor 93 disposed in series with the vibrator 34 in the frequency control circuit or the current (I) flowing through the fixed resistor 93 is measured, amplified by an amplifier 95, and sent to an extreme value detecting means 96. The extreme value detecting means 96 detects the voltage (V) or the current (I) representing the output voltage or the output current of the vibrator 34 in accordance with the sweep frequency. For example, the relationship between the voltage (V) or the current (I) and the sweep frequency becomes as indicated by the solid line in FIG. 8. Though the relationship between the voltage (V) and the frequency is shown in FIG. 8, the voltage and the current are proportional to each other, and therefore the current may be employed instead of the voltage. As shown in FIG. 8, from the relationship with the natural frequencies of the vibration transmitting plate 32, the nozzle body 33 and the application tip 35, the voltage (V) has the maximum value Q and the minimum value P at specific frequencies.

In the case where the lower end of the application tip 35 is not in contact with the surface of the sample solution, the positions of the maximum value Q and the minimum value P are constant regardless of the vertical movement of the sample application arm 30. However, when the lower end of the application tip 35 contacts the surface of the sample solution, the resonance point is caused to change by resistance of the sample solution, and therefore the voltage (V) changes with respect to the frequency as indicated by the broken line in FIG. 8 for example. Thus the maximum value Q and the minimum value P shift to Q' and P'. Accordingly, the extreme value detecting means 96 stores the maximum value Q and the minimum value P at the time the lower end of the application tip 35 is not in contact with the surface of the sample solution, and continuously detects the extreme values as long as the sample application arm 30 is being moved down by the vertical tip position control means 60. Also, a comparison circuit 97 compares the extreme values detected by the extreme value detecting means 96 with the extreme values stored in the extreme value detecting means 96. In this manner, contact of the lower end of the application tip 35 with the surface of the sample solution is detected on the basis of changes in the extreme values, and the liquid level of the sample solution is thus detected. On the basis of detection of contact of the lower end of the application tip 35 with the surface of the sample solution, operation control signals are sent from motor operation control circuits 98 and 99 to the pulse motor 61 of the vertical tip position control means 60 and the piston drive motor 81 of the suction and discharge means 80, thereby to control the vertical movement of the sample application arm 30, suction of the sample solution into the application tip 35 and discharging of the sample solution therefrom.

The vertical tip position control means 60 is constituted in the same manner as in FIG. 3. As in the case of the rotation shaft 55a of the sample application arm 55 in FIG. 3, the rotation shaft 31b of the sample application arm 30 is coupled with the upper portion of the driven member 64 so that they can rotate with respect to each other. Therefore, when the drive member 63 is rotated by the pulse motor 61, the driven member 64 is moved vertically, and the rotation shaft 31b of the sample application arm 30 coupled with the driven member 64 is also moved vertically.

The tip movement means 70 is also constituted in the same manner as in FIG. 3. The driven gear 74 is coaxially secured to the rotation shaft 31b of the sample application arm 30. The rotation shaft 31b of the sample application arm 30 is rotatably supported on the main body 10, and is rotated in the same manner as the rotation shaft 55a in FIG. 3 to rotate the sample application arm 30 so that the application tip 35 fitted to the leading end of the sample application arm 30 is moved between the sucking position and the sample applying position.

Also, the suction and discharge means 80 is constituted in the same manner as in FIG. 3. The flexible hose 87 makes the space 86 in the cylinder 85 communicate with the passage 31a formed in the sample application 30 and communicating with the space 35a in the application tip 35 via the hose 36 and the nozzle body 33. The changes in the volume of the space 86 are transmitted to the space 35a in the application tip 35 via the flexible hose 87 and the passage 31a in the sample application arm 30. In this manner, suction of the sample solution into the space 35a in the application tip 35 and discharging of the sample solution therefrom are carried out.

The operations of the automatic sample applying apparatus 50 shown in FIG. 6 will be described hereinbelow. First, the sample vessel 52 containing the sample solution is disposed at a predetermined position, and the vibrator 34 is made to oscillate by the signal received from the frequency control circuit of the controller 90. Then, the vertical tip position control means 60 is activated to move down the application tip 35 fitted to the leading end of the sample application arm 30 together with the sample application arm 30 at the sucking position. When the application tip 35 is moved down by a predetermined distance and the lower end of the application tip 35 contacts the surface of the sample solution contained in the sample vessel 52, the extreme values P and Q of the output voltage (V) of the vibrator 34 change to P' and Q' as shown in FIG. 8. Therefore, contact of the application tip 35 with the sample solution can be detected reliably by detecting the changes in the extreme values. Since the extents of the changes of the extreme values P' and Q' with respect to the original extreme values P and Q vary in accordance with the depth of insertion of the lower end of the application tip 35 into the sample solution, it is possible to detect the depth of insertion on the basis of the extents of changes of the extreme values P' and Q'. In this case, even if bubbles should be present on the surface of the sample solution and the liquid level of the sample solution is not visible easily for example, contact of the lower end of the application tip 35 with the sample solution can be detected reliably.

Thereafter, the application tip 35 is moved down by a predetermined distance h from the position at which it contacts the surface of the sample solution, and thus the lower end of the application tip 35 is inserted into the sample solution by the predetermined depth h. Then, the suction and discharge means 80 is activated to move the piston 84a and suck a predetermined amount of the sample solution into the space 35a of the application tip 35.

After the predetermined amount of the sample solution has been sucked into the space 35a inside of the application tip 35, the sample application arm 30 is moved up by the vertical tip position control means 60 and the application tip 35 is raised. Then, the sample application arm 30 is rotated around the rotation shaft 31b by the tip movement means 70, and the application tip 35 is moved from the sucking position to the sample applying position. The application tip 35 is then moved down by the vertical tip position control means 60 until the lower end of the application tip 35 comes above and near a reagent layer portion of the chemical analysis slide 1. The sample solution in the application tip 35 is then gradually discharged by the action of the suction and discharge means 80, and a droplet of the sample solution is formed at the lower end of the application tip 35. The application tip 35 is moved down in this condition, and the droplet of the sample solution is applied to the reagent layer portion of the chemical analysis slide 1. Thereafter, the application tip 35 is moved up, and the application of the sample solution is completed.

Figure 9:
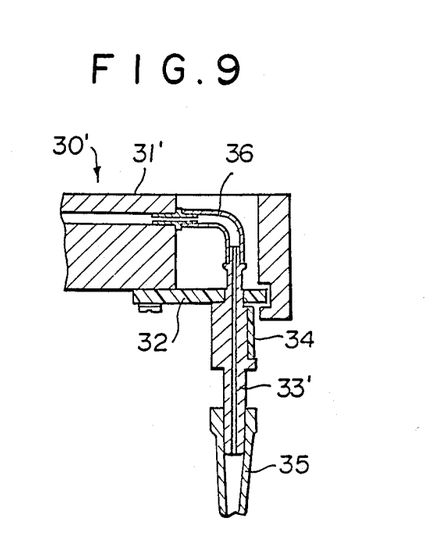
Figure 10:
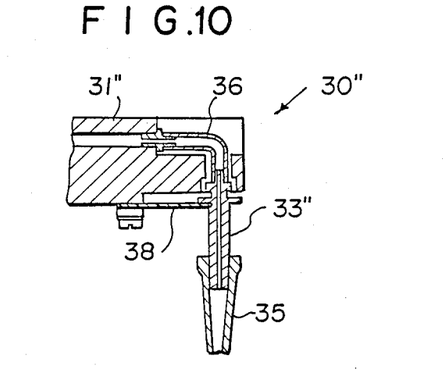

In the embodiment shown in FIG. 6, the vibrator 34 is provided on the vibration transmitting plate 32. Instead, as shown in FIG. 9, the vibrator 34 may be secured to a nozzle body 33' to apply vibration directly to the nozzle body 33' supported on the vibration transmitting plate 32. Or, as shown in FIG. 10, a nozzle body 33'' may be supported by a piezo-electric actuator 38 comprising a vibration transmitting plate and a vibrator formed integrally with each other, and the piezo-electric actuator 38 may be made to vibrate.

Figure 11:
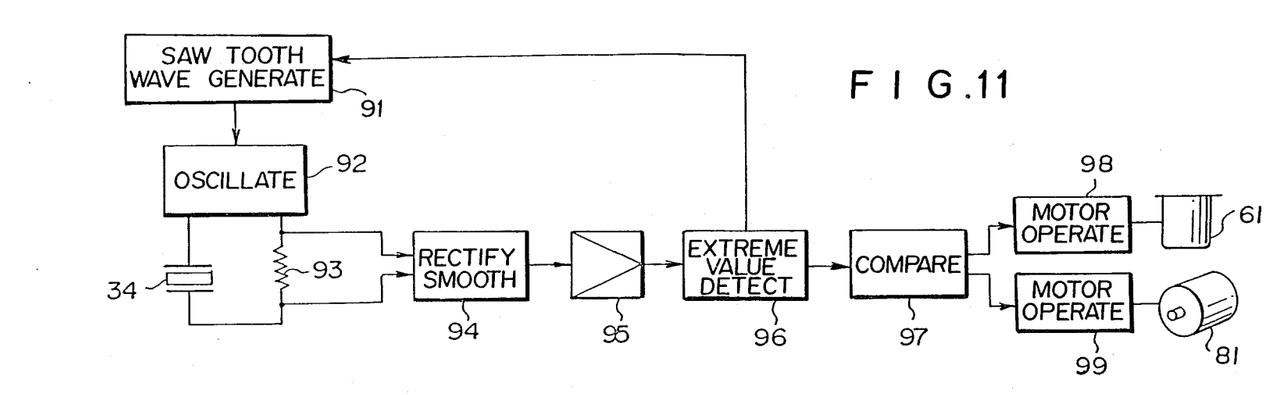
FIG. 11 is a block diagram showing the operation of a controller used in a further embodiment of the liquid level detecting device in accordance with the present invention.

A further example of the automatic sample applying apparatus 50 constituting the chemical analysis apparatus shown in FIG. 1 and provided with a further embodiment of the liquid level detecting device in accordance with the present invention will hereinbelow be described with reference to FIGS. 6, 11, 12 and 13. In the automatic sample applying apparatus 50 having the configuration as shown in FIG. 6, the controller 90 for feeding an electric signal to the vibrator 34 operates as shown in FIG. 11. In FIG. 11, similar elements are numbered with the same reference numerals with respect to FIG. 7, except for a saw tooth wave generator 91.

Figure 12:
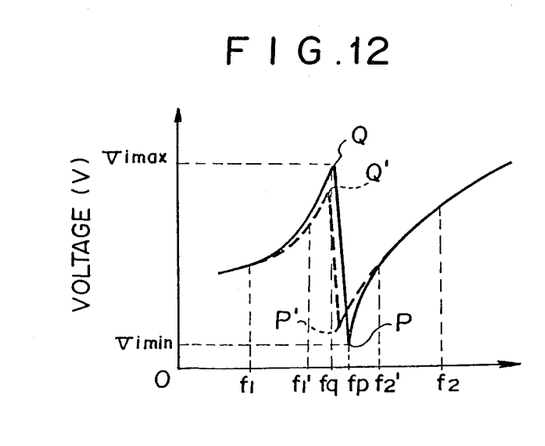
FIG. 12 is a graph showing the relationship between the frequency and the voltage detected in said further embodiment of the liquid level detecting device.

In FIG. 11, the saw tooth wave generator 91 outputs the electric signal in the form of, for example, a sine wave to the vibrator 34 via the voltage control oscillator 92 so that the vibrator 34 vibrates with the frequency thereof changing to sweep within a predetermined frequency range. Specifically, a vibration imparting and frequency control circuit is constituted by the saw tooth wave generator 91, the voltage control oscillator 92 and the vibrator 34 as shown in FIG. 11. When the vibrator 34 vibrates in this manner, the voltage (V) across the ends of a fixed resistor 93 disposed in series with the vibrator 34 in the frequency control circuit is measured. The voltage (V) is rectified and smoothed by a rectifying and smoothing circuit 94, amplified by the amplifier 95, and sent to the extreme value detecting means 96. The extreme value detecting means 96 detects the output voltage (V) of the vibrator 34 in accordance with the sweep frequency. For example, the relationship between the voltage (V) and the sweep frequency becomes as indicated by the solid line in FIG. 12. Though the relationship between the voltage (V) and the frequency is shown in FIG. 12, the voltage and the current are proportional to each other, and therefore the current may be employed instead of the voltage. As shown in FIG. 12, from the relationship with the natural frequencies of the vibration transmitting plate 32, the nozzle body 33 and the application tip 35, the voltage (V) has the maximum value Q and the minimum value P at specific frequencies.

In the case where the lower end of the application tip 35 is not in contact with the surface of the sample solution, the positions of the maximum value Q and the minimum value P are constant regardless of the vertical movement of the sample application arm 30. However, when the lower end of the application tip 35 contacts the surface of the sample solution, the resonance point is caused to change by resistance of the sample solution, and therefore the voltage (V) changes with respect to the frequency as indicated by the broken line in FIG. 12 for example. Thus the maximum value Q and the minimum value P shift to Q' and P' Accordingly, the extreme value detecting means 96 stores the maximum value Q and the minimum value P at the time the lower end of the application tip 35 is not in contact with the surface of the sample solution, and continuously detects the extreme values as long as the sample application arm 30 is being moved down by the vertical tip position control means 60. Also, the comparison circuit 97 compares the extreme values detected by the extreme value detecting means 96 with the extreme values stored in the extreme value detecting means 96. In this manner, contact of the lower end of the application tip 35 with the surface of the sample solution is detected on the basis of changes in the extreme values, and the liquid level of the sample solution is thus detected. In this case, the sweep frequency range in the first sweep is adjusted to be comparatively wide, and the extreme values P and Q are detected reliably regardless of variations in the frequencies corresponding to the extreme values caused by differences in the shape of the application tip 35, variations in the size of the application tip 35, and variations in the sizes of the piezo-electric element, the tip fitting mechanism and the like. After the extreme values P and Q are detected in this manner, they are fed back from the extreme value detecting means 96 to the saw tooth wave generator 91. In the second sweep and after, the sweep range is contracted to a narrow range including the frequencies corresponding to the extreme values P and Q, and detection of the extreme values is carried out within the contracted sweep range. Therefore, the sweep time and the time required for detection of the liquid level become short. On the basis of detection of contact of the lower end of the application tip 35 with the surface of the sample solution, operation control signals are sent from the motor operation control circuits 98 and 99 to the pulse motor 61 of the vertical tip position control means 60 and the piston drive motor 81 of the suction and discharge means 80, thereby to control the vertical movement of the sample application arm 30, suction of the sample solution into the application tip 35 and discharging of the sample solution therefrom.

Figure 13:
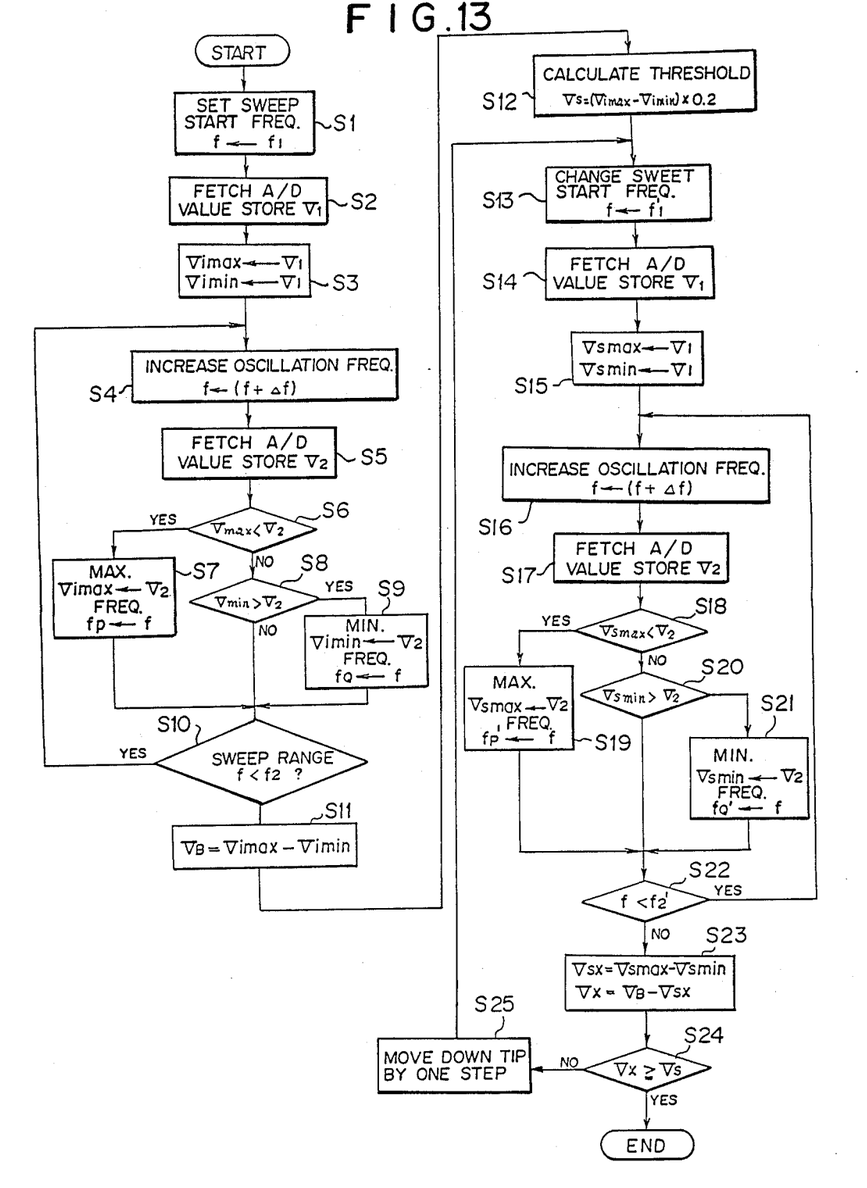
FIG. 13 is a flow chart showing the control by the controller shown in FIG. 11.

The operations of the automatic sample applying apparatus 50 constituted in the aforesaid manner will now be described with reference to FIG. 13. First, the sample application arm 30 is disposed at the sucking position so that the application tip 35 is positioned above the sample vessel 52 containing the sample solution. Then, in a step S1, the sweep start frequency is adjusted to f1, and the vibrator 34 is made to oscillate at the frequency f1. In a step S2, an output voltage V1 of the vibrator 34 at this time is detected and stored. Also, in a step S3, the value V1 is read out as Vimax and Vimin. Then, the oscillation frequency is increased by a predetermined minute value $\Delta f$ in a step S4, and an output voltage V2 of the vibrator 34 in the course of oscillation at the increased frequency is detected and stored in a step S5. A step S6 is then carried out to judge whether the voltage V2 is higher than Vimax or not. In the case where the voltage V2 is higher than Vimax, the operation sequence is advanced to a step S7 for fetching the value V2 as Vimax and fetching the frequency f at this time as fp. On the other hand, in the case where the voltage V2 is lower than Vimax, the operation sequence is advanced to a step 8 for judging whether the voltage V2 is lower than Vimin or not. In the case where the voltage V2 is lower than Vimin, the operation sequence is advanced to a step S9 for fetching the value V2 as Vimin and fetching the frequency f at this time as fq. Thereafter, a step S10 is carried out for judging whether the vibration frequency f is lower than the upper limit value f2 of the sweep range. In the case where the vibration frequency f is lower than the upper limit value f2, i.e. when the vibration frequency f is still within the sweep range, the operation sequence returns to the step S4, and the operations from the step S4 to the step S9 are repeated until the frequency comes up to the upper limit value f2. In this manner, sweep is carried out within the range from the frequency f1 to the frequency f2 in FIG. 12, the changes in the voltage as indicated by the solid line are detected, and the maximum value Q and the minimum value P are detected.

Then, in a step S11, the difference (Vimax−Vimin) between the voltages at the extreme values Q and P is read and stored as VB. In a step S12, a value calculated by the formula expressed as (Vimax−Vimin)×0.2 is stored as a threshold value Vs.

Thereafter, on the basis of the frequencies fp and fq corresponding to the points P and Q detected as the extreme values in the course of the operations from the step S4 to the step S10, a sweep range (the range from f1' to f2') narrower than the aforesaid sweep range (the range from f1 to f2) and including the frequencies fp and fq is set. A step S13 is then carried out for vibrating the vibrator 34 at the frequency f1' as the sweep start frequency in said narrower sweep range. Also, in steps S14 and S15, the output voltage V1 of the vibrator 34 at this time is fetched, and the value V1 is fetched as Vsmax and Vsmin. Then, steps S16 and S17 are carried out for increasing the oscillation frequency f by $\Delta f$, and fetching the output voltage V2 of the vibrator 34 at the increased frequency. A step S18 is then carried out to judge whether the voltage V2 is higher than Vsmax or not. In the case where the voltage V2 is higher than Vsmax, the value V2 is fetched as Vsmax, and the frequency f at this time is fetched as fp'. On the other hand, in the case where the voltage V2 is lower than Vsmax, the operation sequence is advanced to a step S20 for judging whether the voltage V2 is lower than Vsmin or not. In the case where the voltage V2 is lower than Vsmin, the operation sequence is advanced to a step S21 for fetching the value V2 as Vsmin and fetching the frequency f at this time as fq'. Thereafter, a step S22 is carried out for judging whether the vibration frequency f is lower than the upper limit value f2' of the sweep range. In the case where the vibration frequency f is lower than the upper limit value f2', i.e. when the vibration frequency f is still within the sweep range, the operation sequence returns to the step S13, and the operations from the step S13 to the step S22 are repeated until the frequency comes up to the upper limit value f2'.

In this manner, the maximum value and the minimum value in the course of the sweep within the sweep range from f1' to f2' are detected. Then, in a step S23, Vsx is calculated by the formula expressed as (Vsmax−Vsmin), and the difference (VB−Vsx) between the voltage difference VB calculated in the step S11 and the value Vsx is calculated to obtain a value Vx. The value Vx represents the difference between (a) the difference between the output voltages at the maximum value point and the minimum value point in the course of the first sweep detected in the steps S4 through S10, and (b) the difference between the output voltages at the maximum value point and the minimum value point detected in the course of the sweep within the narrowed sweep range in the steps S13 through S22. A step S24 is then carried out to judge whether said difference is larger than the threshold level Vs or not, i.e. whether the maximum value point and the minimum value point have changed by a value not less than a predetermined value or not. In the case where said difference is smaller than the threshold level Vs, i.e. in the case where the changes in the extreme values are not so large, since the lower end of the application tip 35 has not yet contacted the sample solution, the operation sequence is advanced to a step S25 for moving down the sample application arm 30 and the application tip 35 by a single step, and is returned to the step S13. Thereafter, the operations from the step S13 to the step S25 are repeated until Vx becomes larger than Vs, and the application tip 35 contacts the sample solution or the lower end of the application tip 35 is inserted by a predetermined distance into the sample solution. In this manner, contact of the application tip 35 with the sample solution or insertion of the lower end of the application tip 35 by a predetermined distance into the sample solution can be detected reliably. In this case, since after the first sweep the sweep range is narrowed, the time required for the sweep becomes short, and contact of the application tip 35 with the sample solution can be detected quickly.

In the aforesaid embodiments, a sine wave-like electric signal should preferably be fed from the saw tooth wave generator 91 via the voltage control oscillator 92 in the manner as shown in FIG. 11 to the vibrator 34 so that the vibrator 34 vibrates in the sine wave form with the frequency thereof changing to sweep within a predetermined frequency range, for example, within the range of 0 to 1 kHz. (Specifically, the amplitude of the vibrator 34 becomes a sine function of time.) In this case, since sine wave-like vibration is applied by the vibrator 34, the changes in the aforesaid extreme values become larger than in the case where other vibration waves, for example, rectangular waves or triangular waves, are applied. Therefore, the liquid level can be detected easily.

In the aforesaid embodiments, the liquid level detecting device is constituted for detecting contact of the application tip 53 or the application tip 35 with the sample solution and detecting the liquid level of the sample solution in the automatic sample applying apparatus 50 for automatically applying the sample solution to the reagent layer of the chemical analysis slide. However, the liquid level detecting device in accordance with the present invention is not limited to the aforesaid embodiments, and is applicable also to detection of liquid levels of various liquids.

We claim:

1. In a sample solution sucking apparatus comprising a sample vessel containing a sample solution, a suction member disposed above the sample vessel and having a suction opening at a lower end, a vertical position control means for vertically moving the suction member, and a suction means communicating with the suction member for sucking the sample solution via the suction opening when the suction member is moved down by the vertical position control means and the lower end of the suction member is inserted into the sample solution, a liquid level detecting device comprising:
 (i) a vibration imparting means for imparting vibration to said sample vessel, and
 (ii) a piezo-electric element provided on one of said suction member and said suction means,
whereby a change in an output voltage of said piezo-electric element is read out as said suction member is moved vertically by said vertical position control means, contact of the lower end of said suction member with said sample solution is detected on the basis of the change in said output voltage, and the liquid level of said sample solution is detected.

2. A liquid level detecting device as defined in claim 1 wherein said sample solution contains a substance, which is to be measured, and is to be applied onto a reagent layer of a chemical analysis slide, said suction member is an application tip fitted to a leading end of said suction means, and said change in the output voltage of said piezo-electric element provided on the leading end of said suction means is read out to detect contact of a lower end of said application tip with said sample solution.

3. In a sample solution sucking apparatus comprising a sample vessel containing a sample solution, a suction member disposed above the sample vessel and having a nozzle member for suction at a lower end, a vertical position control means for vertically moving the suction member, and a suction means communicating with the nozzle member for sucking the sample solution via the nozzle member when the suction member is moved down by the vertical position control means and the nozzle member at the lower end of the suction member is inserted into the sample solution, a liquid level detecting device comprising:
 (i) a vibration transmitting plate for holding said nozzle member to said suction member and capable of being vibrated,
 (ii) a vibration imparting means for imparting vibration having a predetermined frequency to said nozzle member held by said vibration transmitting plate,
 (iii) a frequency control circuit for changing the frequency of vibration imparted by said vibration imparting means to said nozzle member, and
 (iv) an extreme value detecting means for detecting one of an output voltage and an output current of said vibration imparting means and detecting an extreme value one of said output voltage and said output current corresponding to changes in said frequency,
whereby contact of said nozzle member with said sample solution is detected on the basis of a change in the extreme value detected by said extreme value detecting means, and the liquid level of said sample solution is detected.

4. A liquid level detecting device as defined in claim 3 wherein said sample solution contains a substance, which is to be measured, and is to be applied onto a reagent layer of a chemical analysis slide, said nozzle member for suction is composed of a nozzle body connected to said suction means and an application tip fitted to a leading end of said nozzle body, and contact of a lower end of said application tip with said sample solution is detected on the basis of said change in the extreme value.

5. A liquid level detecting device as defined in claim 3 or 4 wherein said vibration imparting means is provided on said vibration transmitting plate, and vibration is imparted to said nozzle member via said vibration transmitting plate.

6. A liquid level detecting device as defined in claim 3 or 4 wherein said vibration imparting means is provided on said nozzle member.

7. A liquid level detecting device as defined in claim 3 or 4 wherein said vibration imparting means and said vibration transmitting plate are formed integrally with each other.

8. In a sample solution sucking apparatus comprising a sample vessel containing a sample solution, a suction member disposed above the sample vessel and having a nozzle member for suction at a lower end, and a vertical position control means for vertically moving the suction member, a liquid level detecting device comprising:
(i) a vibration transmitting plate for holding said nozzle member to said suction member and capable of being vibrated,
(ii) a vibration imparting means for imparting vibration having a predetermined frequency to said nozzle member held by said vibration transmitting plate.
(iii) a frequency control circuit for operating said vibration imparting means to impart vibration sweeping within a predetermined frequency range,
(vi) an extreme value detecting means for detecting changes in one of an output voltage value and output current value of said vibration imparting means and detecting an extreme value of said one output value corresponding to changes in the frequency within said predetermined frequency range, and
(v) a sweep range contracting means for having the extreme value of the impedance of said vibration imparting means detected by having a sweep within a comparatively wide frequency range done by said frequency control circuit before said nozzle member contacts said sample solution, and contracting said predetermined frequency range, within which the vibration sweeping is effected by said frequency control circuit, to a narrow range including a frequency corresponding to said detected extreme value,
whereby contact of said nozzle member with said sample solution is detected and the liquid of said sample solution is detected on the basis of a change in the extreme value detected based on said one output value of said vibration imparting means at the time vibration sweeping within said narrow frequency range contracted by said sweep range contracting means is imparted.

9. A liquid level detecting device as defined in claim 8 wherein said sample solution contains a substance, which is to be measured, and is to be applied onto a reagent layer of a chemical analysis slide, said nozzle member for suction is composed of a nozzle body connected to a suction means and an application tip fitted to a leading end of said nozzle body, and contact of a lower end of said application tip with said sample solution is detected on the basis of said change in the extreme value.

10. A liquid level detecting device as defined in claim 8 or 9 wherein said vibration imparting means is provided on said vibration transmitting plate, and vibration is imparted to said nozzle member via said vibration transmitting plate.

11. In a sample solution sucking apparatus comprising a sample vessel containing a sample solution, a suction member disposed above the sample vessel and having a nozzle member for suction at a leading end, and a vertical position control means for vertically moving the suction member, a liquid level detecting device comprising:
(i) a vibration transmitting plate for holding said nozzle member to said suction member and capable of being vibrated,
(ii) a vibration imparting means for imparting sine wave like vibration having a predetermined frequency to said nozzle member held by said vibration transmitting plate,
(iii) a frequency control circuit for changing the frequency of vibration imparted by said vibration imparting means to said nozzle member,
(iv) an extreme value detecting means for detecting changes in one of output voltage value and output current value of said vibration imparting means and detecting an extreme value of said one output value corresponding to changes in said frequency, and
(v) a contact detecting means for detecting contact of said nozzle member with said sample solution on the basis of a change in the extreme value detected by said extreme value detecting means, and detecting the liquid level of said sample solution.

12. A liquid level detecting device as defined in claim 11 wherein said sample solution contains a substance, which is to be measured, and is to be applied onto a reagent layer of a chemical analysis slide, said nozzle member for suction is composed of a nozzle body connected to a suction means and an application tip fitted to a leading end of said nozzle body, and contact of a lower end of said application tip with said sample solution is detected on the basis of said change in the extreme value.

13. A liquid level detecting device as defined in claim 11 or 12 wherein said vibration imparting means is provided on said vibration transmitting plate, and vibration is imparted to said nozzle member via said vibration transmitting plate.

* * * * *